(12) United States Patent
Haga

(10) Patent No.: US 8,712,699 B2
(45) Date of Patent: Apr. 29, 2014

(54) AGGLUTINATION JUDGMENT METHOD

(75) Inventor: Tadashi Haga, Mishima (JP)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 12/466,048

(22) Filed: May 14, 2009

(65) Prior Publication Data

US 2009/0287419 A1 Nov. 19, 2009

Related U.S. Application Data

(63) Continuation of application No. PCT/JP2007/072217, filed on Nov. 15, 2007.

(30) Foreign Application Priority Data

Nov. 15, 2006 (JP) .................................. 2006-309366

(51) Int. Cl.
G01N 33/48 (2006.01)
G06F 19/00 (2011.01)

(52) U.S. Cl.
USPC .................................. 702/21; 702/19; 436/164

(58) Field of Classification Search
USPC ........................ 702/19, 21; 436/164; 382/173
See application file for complete search history.

(56) References Cited

U.S. PATENT DOCUMENTS

| 5,389,555 | A  | * | 2/1995  | Watanabe et al.        | 436/164  |
|-----------|----|---|---------|------------------------|----------|
| 5,541,417 | A  | * | 7/1996  | Xiong et al.           | 250/559.05 |
| 6,498,863 | B1 | * | 12/2002 | Gaidoukevitch et al.   | 382/173  |
| 2002/0168784 | A1 | * | 11/2002 | Sundrehagen et al.  | 436/536  |

FOREIGN PATENT DOCUMENTS

| JP | 56-2561     |   | 1/1981  |
|----|-------------|---|---------|
| JP | 63-256839   |   | 10/1988 |
| JP | 63256839 A  | * | 10/1988 |
| JP | 3-165429    |   | 7/1991  |
| JP | 4-72547     |   | 3/1992  |
| JP | 4-120442    |   | 4/1992  |
| JP | 2525487     |   | 5/1996  |
| JP | 8-210970    |   | 8/1996  |
| JP | 11-37923    |   | 2/1999  |

* cited by examiner

Primary Examiner — Andrew Schechter
Assistant Examiner — Haidong Zhang
(74) Attorney, Agent, or Firm — Kilpatrick Townsend & Stockton LLP

(57) ABSTRACT

The present invention provides an agglutination judgment method includes a first step of collecting data of a transmitted light intensity from each of measuring points included in a predetermined region of the reaction pattern, a second step of calculating a parameter representing the dispersion of a transmitted light intensity in the region, and a third step of judging the agglutination or non-agglutination by comparing the parameter thus calculated with a predetermined reference value.

5 Claims, 7 Drawing Sheets

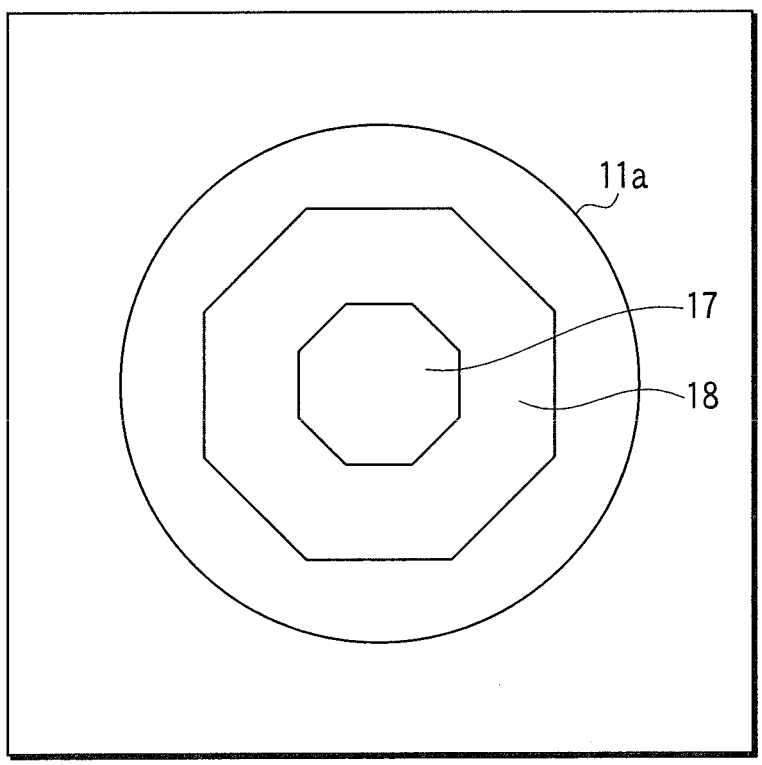
F I G. 2

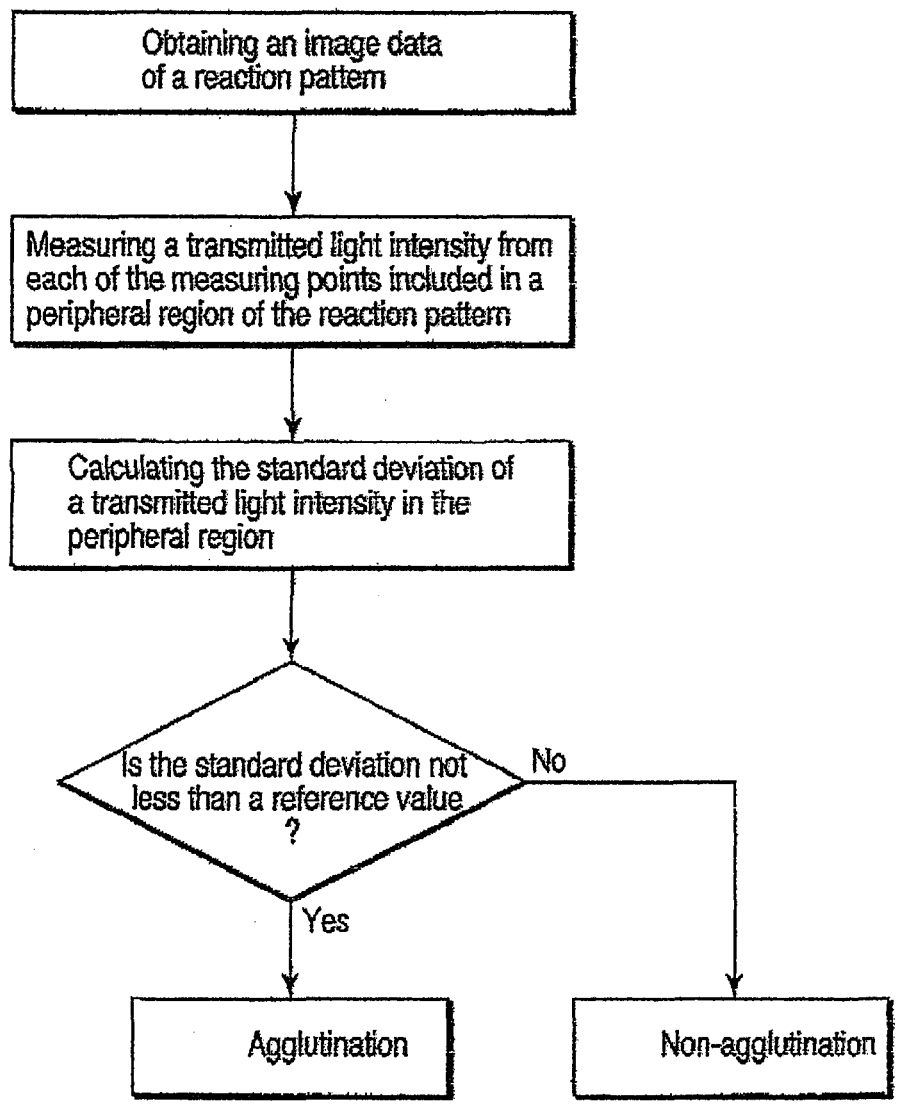
F I G. 7

AGGLUTINATION JUDGMENT METHOD

CROSS REFERENCE TO RELATED APPLICATIONS

This is a Continuation application of PCT Application No. PCT/JP2007/072217, filed Nov. 15, 2007, which was published under PCT Article 21(2) in Japanese.

This application is based upon and claims the benefit of priority from prior Japanese Patent Application No. 2006-309366, filed Nov. 15, 2006, the entire contents of which are incorporated herein by reference.

BACKGROUND OF THE INVENTION

1. Field of the Invention

This invention relates to an agglutination judgment method for automatically judging the agglutination or non-agglutination of particles. In particular, this invention relates to a method of automatically judging the agglutination or non-agglutination of particles by optically measuring a reaction pattern of particles created in a vessel in a clinical test for instance.

2. Description of the Related Art

For the purpose of determining blood type or detecting antigens and antibodies in blood, a method of observing the agglutination of particles is generally used. In this method, blood specimen is dispensed in a reaction vessel and reagent particles are reacted immunologically. From the reaction pattern of the particles created on the bottom of the vessel, it is judged whether the agglutination of the particles occurs or not.

In recent years, this judgment has been mechanically performed. For example, the two-dimensional image of the particle agglutination is taken and the image data subjected to predetermined image processing. From the results of this processing, the agglutination reaction pattern of particles is judged (for example, see Japanese Patent No. 2525487).

However, this automatic judgment technique is accompanied with the problem that it is difficult to detect a weak positive image created by partial agglutination of particles. Herein, the partial agglutination means an agglutination reaction may be brought about in a blood typing test. Generally, the red blood cells which are not agglutinated are allowed to sediment at a central portion of the reaction vessel, thereby forming a "negative image", i.e., a non-agglutinated image. However, if red blood cells differing in antigenicity are mixed with antibody capable of reacting with only one antigenicity of red blood cells, a partially agglutinated image wherein agglutinated red blood cells are mixed with un-agglutinated blood can be formed.

In this partial agglutination, although sedimentation can be observed at a central portion just like the ordinary negative image, agglutinated red blood cells are allowed to exist at the peripheral portion. Although it is possible to easily recognize these agglutinated red blood cells formed at the peripheral portion by visual inspection, this image of agglutinated red blood cells has been judged as negative in the case of the conventional automatic judgment. Therefore, even in the automatic agglutination judgment method, it has been conventionally required to correct the result by visual inspection by the operator, etc.

BRIEF SUMMARY OF THE INVENTION

Therefore, the present invention provides an agglutination judgment method wherein even the partial agglutination can be automatically judged as agglutination, thereby making it possible to obtain a result which is highly reliable.

According to the present invention, there is provided an agglutination judgment method wherein an agglutination reaction pattern created in a vessel is optically measured and, based on data thus measured, agglutination or non-agglutination of the particles is automatically judged, the method comprising: a first step of collecting data of a transmitted light intensity from each of the measuring points included in a predetermined peripheral region of the reaction pattern; a second step of calculating the standard deviation of a transmitted light intensity in the peripheral region; and a third step of judging the reaction pattern as agglutination when the standard deviation calculated is not less than a predetermined reference value and judging the reaction pattern as non-agglutination when the standard deviation calculated is less than the predetermined reference value.

BRIEF DESCRIPTION OF THE SEVERAL VIEWS OF THE DRAWING

FIG. 2 is a diagrammatic illustration showing a C-region 17 and a P-region 18;

FIG. 7 is a flowchart of a process including calculating the standard deviation of a transmitted light intensity in the peripheral region.

DETAILED DESCRIPTION OF THE INVENTION

According to the present invention, there is provided with an agglutination judgment method wherein an agglutination reaction pattern created in a vessel is optically measured and, based on data thus measured, agglutination or non-agglutination of the particles is automatically judged, the method being featured in that, a partial agglutination image is enabled to be automatically judged as an agglutination in addition to a conventional agglutination image (a so-called positive image) where the particles are agglutinated and a weak positive image exhibiting a weak agglutination strength, thereby improving accuracy in the judgment of agglutination reaction pattern.

According to the present invention, conical-shaped reaction vessel is used in the agglutination reaction. For example, a well in a microplate, etc., can be applicable. The creation of the reaction pattern may be achieved by leaving the reaction vessel to stand or by subjecting the reaction vessel to centrifuge.

Figure 1A:
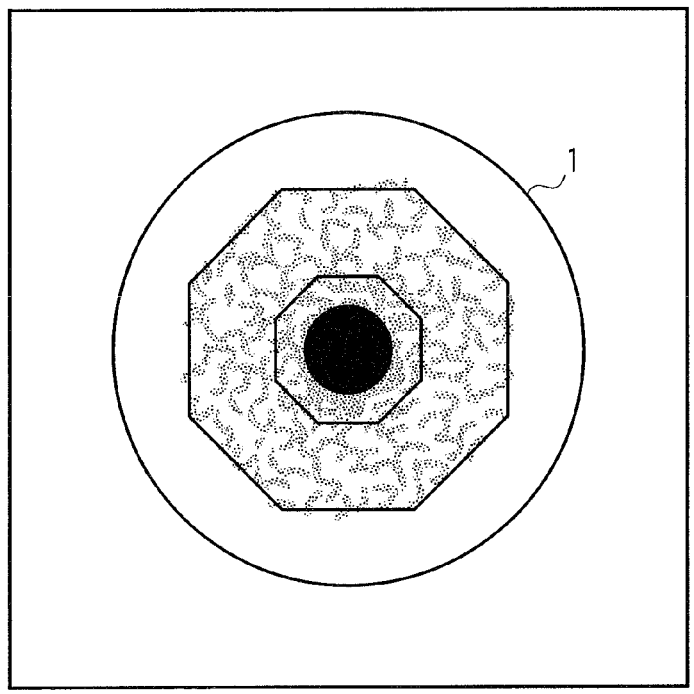
FIG. 1A is a diagrammatic illustration showing partial agglutination image.
Figure 1B:
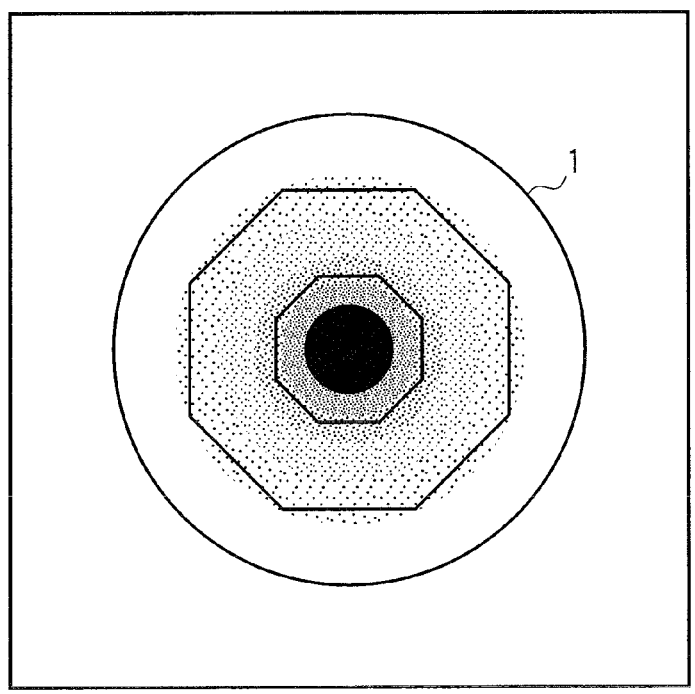
FIG. 1B is a diagrammatic illustration showing non-agglutination image.

FIGS. 1A and 1B are diagrammatic illustration showing the reaction pattern that was formed by leaving a well 1 to stand after a test liquid containing test particles was dispensed in the well 1. FIG. 1A shows a partial agglutination image and FIG. 1B shows a non-agglutination image. As shown in FIG.

1B, the particles which were not agglutinated were allowed to sediment at a central portion of the well, thereby creating a negative image. As shown in FIG. 1A, although the partial agglutination image indicates nearly the same pattern as that of the non-agglutination image, a shadow may be caused by macula in a peripheral region. Although this shadow can be clearly recognized in the visual inspection thereof, it has been conventionally judged as non-agglutination by the automatic judgment using the conventional measurement apparatus.

For example, Japanese Patent No. 3165429 discloses an automatic judgment method wherein the weak positive image is judged as indicating agglutination. In this invention disclosed in this Japanese Patent, by taking advantage of the characteristic of the weak positive image wherein the boundary portion of the test particles which have precipitated at a central portion of the reaction vessel becomes blurry and unclear, the determination of agglutination/non-agglutination is performed on the basis of the rate of change in the transmitted light intensity at the boundary portion between the central region and the peripheral region. Details thereof should be referred to this Japanese Patent No. 3165429. Herein, for the sake of convenience, the rate of change of the transmitted light intensity is called as the sharpness between periphery and center (SPC). When this SPC is smaller than a predetermined value, the reaction patterns are judged as agglutination and when this SPC is equal to or larger than the predetermined value, the particles are judged as non-agglutination.

However, there is a possibility that both of these negative image (non-agglutinated image) and partially agglutinated image may take the same SPC value, thereby making it difficult to accurately judge the partially agglutinated even if this SPC value is applied.

Therefore, in the present invention, in order to accurately judge the partial agglutination, the data of the transmitted light intensity is collected from each of the measuring points included in a predetermined region of the reaction pattern, and a parameter representing the dispersion of the transmitted light intensity in the region is calculated. This parameter is then compared with a reference value which has been predetermined, thereby judging the agglutination or the non-agglutination.

In one embodiment, the predetermined region means a peripheral region of the reaction pattern. Preferably, this predetermined region is a region located on the outside of the central region including the particle sedimentation portion formed at a central portion of the non-agglutination reaction pattern and in which the existence of particles in a trace quantity can be observed.

In another embodiment, the standard deviation of the transmitted light intensity may be suitable for the parameter representing the dispersion of the transmitted light intensity. In a further embodiment, the range indicating a width between the maximum value and the minimum value of the transmitted light intensity may be suitable for the parameter.

In the method of the present invention, the reaction pattern that has been created in a vessel is optically measured as in the case of the conventional method. This measurement should preferably be performed by taking the reaction pattern by means of a CCD camera, for instance. However, the present invention is not limited to such a case. It should be noted that, when the reaction pattern is took by means of a CCD camera, the measurement points are assumed as pixels and hence the measurement points will be explained as pixels in the following description.

In the method of the present invention, the measured data obtained by taking each of the wells is at first subjected to image processing and the judgment of agglutination/non-agglutination is performed according to a conventionally known method. Then, based on the image data of the bottom of the well that has been judged as non-agglutination, the transmitted light intensity of each of every pixel existing within the predetermined peripheral region 18 (P-region) as shown in FIG. 2 is measured. Thereafter, the standard deviation PSD or the range of the transmitted light intensity of every pixels existing within the peripheral region 18 is calculated. The standard deviation can be calculated using the following equation:

$$PSD = \sqrt{\frac{\sum (Xi - Xmean)^2}{n-1}}$$

wherein n indicates the number of pixels; Xi is each of measured values; and Xmean is an average of the measured values.

The standard deviation PSD of the transmitted light intensity in the peripheral region represents the non-uniformity (unevenness) in light intensity in the peripheral region. The standard deviation represents the magnitude of divergence of distribution, so that when the value of the standard deviation is small, it means that the distribution is concentrated and when the value of the standard deviation is large, it means that the distribution is dispersed, i.e., the light intensity is non-uniform. Therefore, when the standard deviation PSD is larger than a predetermined reference value, the transmitted light intensity in the peripheral region may be assumed as non-uniform, thus making it possible to assume the existence of agglutinated red blood cells. Thus, the reaction pattern of the well is judged as agglutination. Alternatively, the reference value may be set such that the reaction pattern can be judged as agglutination when the standard deviation is not less than the reference value. This reference value may be optionally set by an operator by taking into consideration the kind of the test substance, the reaction conditions and the configuration of the reaction vessel.

The peripheral region 18 (P-region) and the central region 17 (C-region) may be optionally determined. The C-region should preferably be set in such a manner that the sedimentation image of particles to be observed at the central portion of the reaction pattern can be completely encircled by the C-region. The P-region should preferably be set at such a region that a trace amount of particles existing outside the C-region can be observed.

In the foregoing description, there has been explained one embodiment wherein the judgment of partial agglutination is performed according to the present invention after the judgment of the agglutination or non-agglutination has been judged according to the conventionally known method. However, as another embodiment, the judgment of the weak positive image may be performed together with the judgment of the partial agglutination. Further, all of these judgments may be performed concurrently or sequentially.

Figure 3:
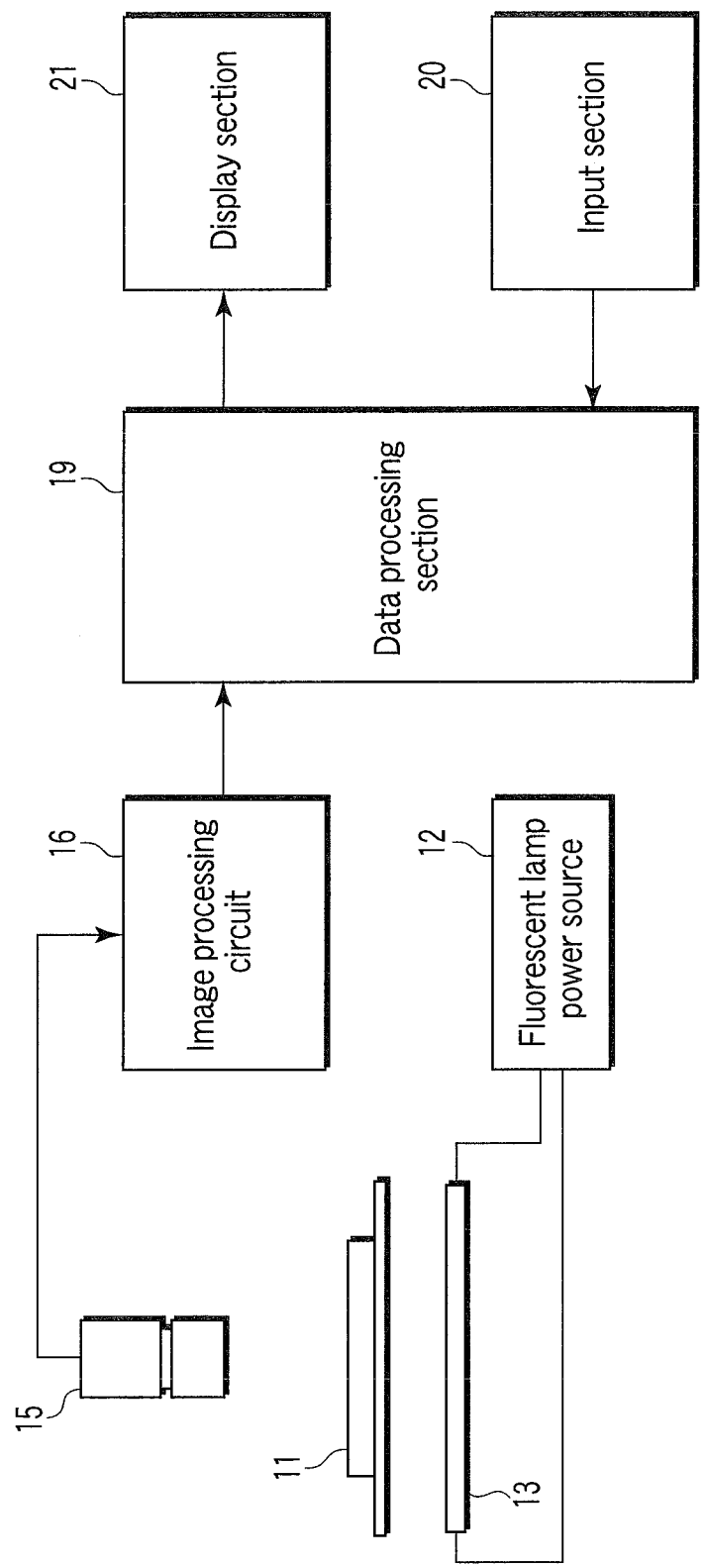
FIG. 3 is a block diagram illustrating the construction of an automatic agglutination image judgment apparatus representing one embodiment.
Figure 4:
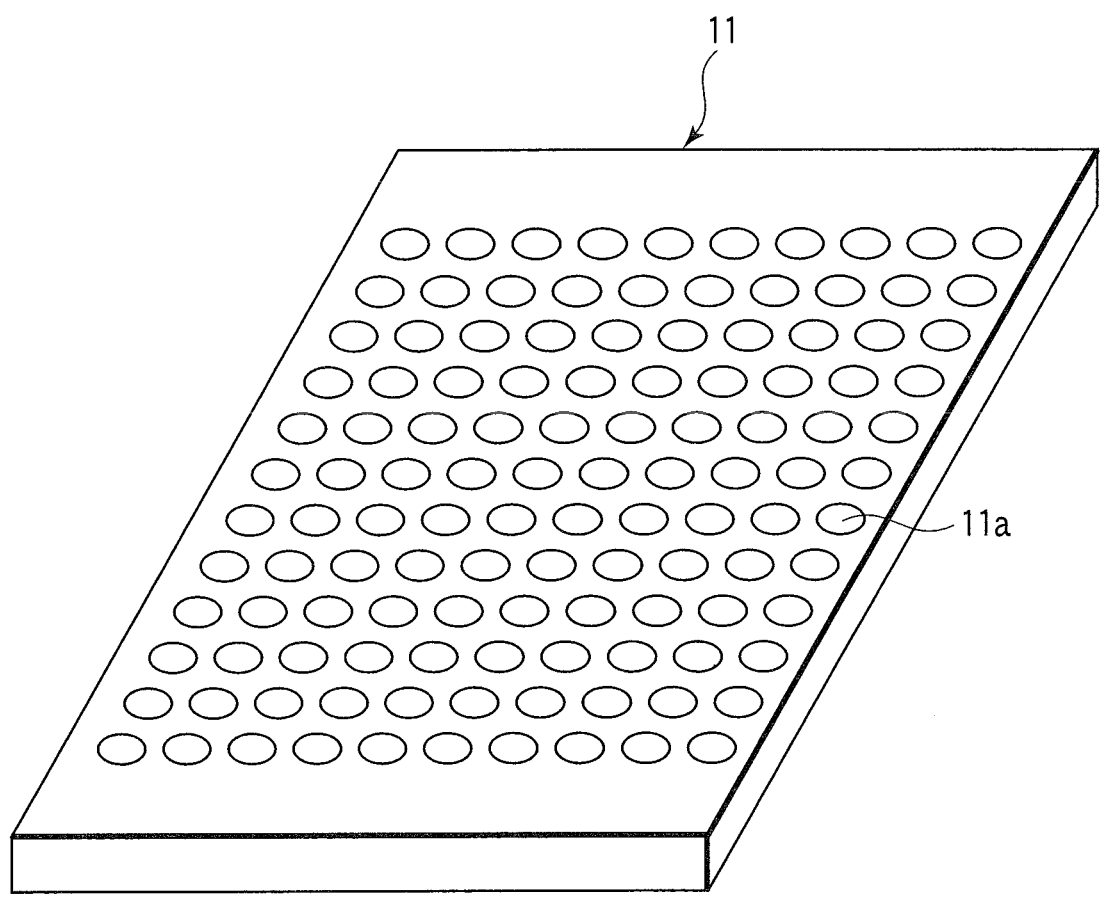
FIG. 4 is a view illustrating the construction of the microplate 11 shown in FIG. 3.

FIG. 3 shows a block diagram illustrating the construction of one example of the automatic agglutination image judgment apparatus used in carrying out the present invention. In this embodiment, a microplate 11 is used as a reaction vessel. This microplate 11 is illuminated from the bottom side thereof by means of a fluorescent lamp 13 electrically connected to a power source 12. As shown in FIG. 4, this microplate 11 is provided with a large number of wells 11a arrayed as a matrix pattern, each well having a conical-shaped bottom. A test liquid containing test particles is dispensed in each of these wells 11a and is left to stand according to the standing method so as to create a reaction pattern on the bottom of the well.

This image created on the bottom of each of the wells 11a of the microplate 11 is illuminated by the fluorescent lamp 13 and took successively by means of a CCD camera 15 to obtain image data. The image data is supplied to an image processing circuit 16, in which, based on the input image data, the measurement of the transmitted light intensity is performed with respect to all of pixels locating within the peripheral region of the bottom view of the well 11a. It should be noted that the image data of each wells 11a is successively acquired by relatively moving the microplate 11 and the CCD camera 15 two-dimensionally in the horizontal plane.

Next, the data processing in this image processing circuit 16 will be explained as one example wherein the standard deviation PSD is applied.

In this image processing circuit 16, based on the input image data of each wells 11a that has been supplied by the CCD camera 15, the data of the transmitted light intensity at each of the pixels in the peripheral region 18 of the well that has been set in advance as shown in FIG. 2 is acquired at first and the standard deviation PSD of the transmitted light intensity in this peripheral region is calculated.

The standard deviation PSD that has been calculated is supplied to a data processing circuit 19 in which the standard deviation PSD is compared with a reference value to thereby judge the agglutination or the non-agglutination. The results of this judgment are displayed on a display section 21, for example, in response to the instruction from an input section 20 such as a keyboard.

As described above, since the data of the transmitted light intensity in the peripheral region of the reaction pattern is extracted from the image data of the bottom of the well 11a to calculate the standard deviation thereof and the agglutination/non-agglutination of the reaction pattern is judged on the basis of the value of this calculated standard deviation, there is no possibility of mistaking the partial agglutination for the non-agglutination, thus making it possible to accurately judge the partial agglutination and to obtain judgment results excellent in reliability. Therefore, since it is no longer required to check and correct the judgment results by visual inspection by an operator or by other means as conducted in the prior art, the burden on an operator can be greatly alleviated.

It should be noted that, in this example, the image data of the bottom of each of the wells 11a of the microplate 11 is successively acquired by relatively moving the microplate 11 and the CCD camera 15 two-dimensionally in the horizontal plane. However, it is also possible to apply a method wherein an entire image of the microplate 11 is acquired and the image data of the bottom of each of the wells 11a extracted from the data of this image, the extracted data being subsequently processed in the same manner as described above.

Figure 5:
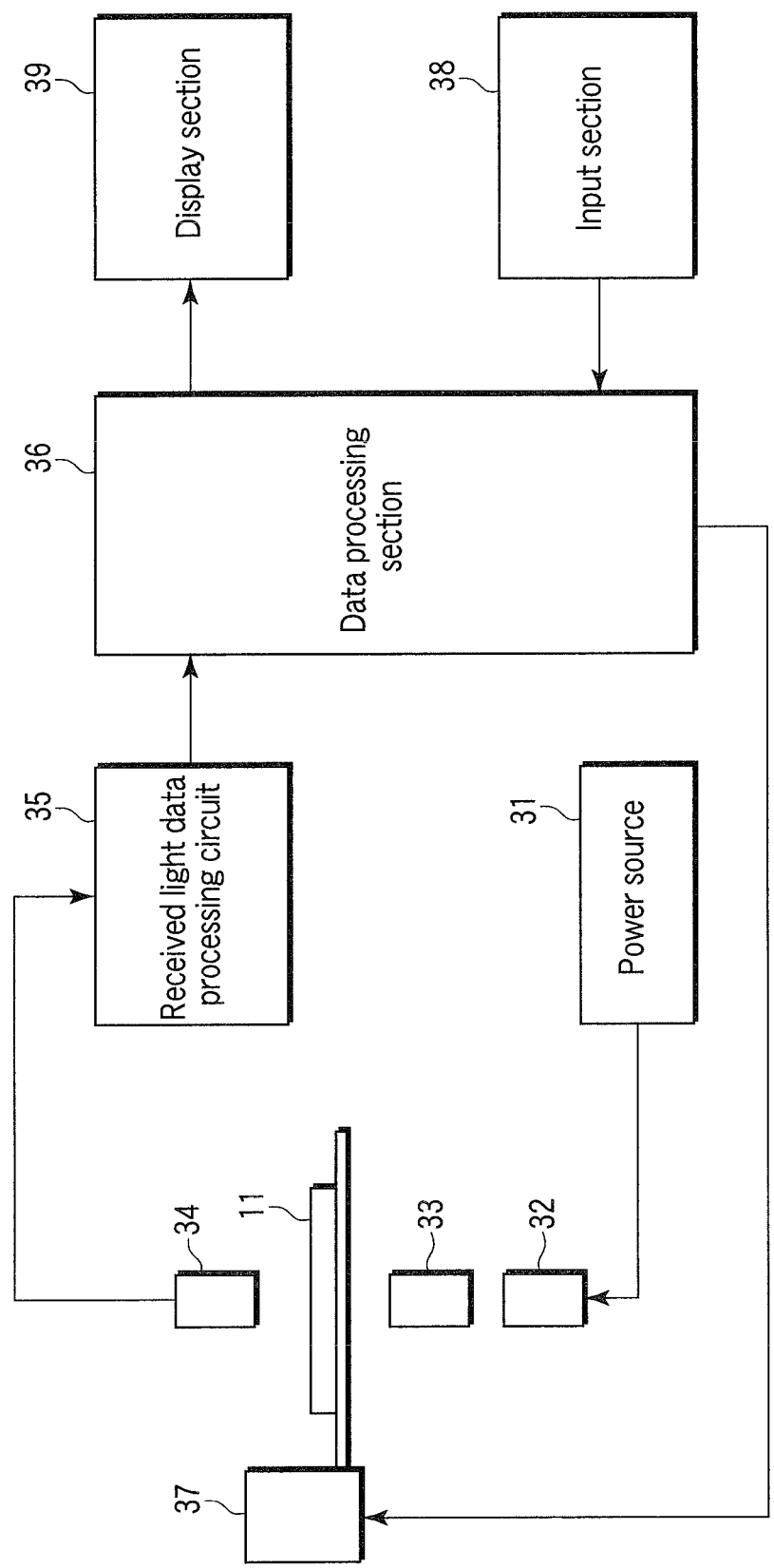
FIG. 5 is a block diagram illustrating the construction of an automatic agglutination image judgment apparatus representing another embodiment
Figure 6:
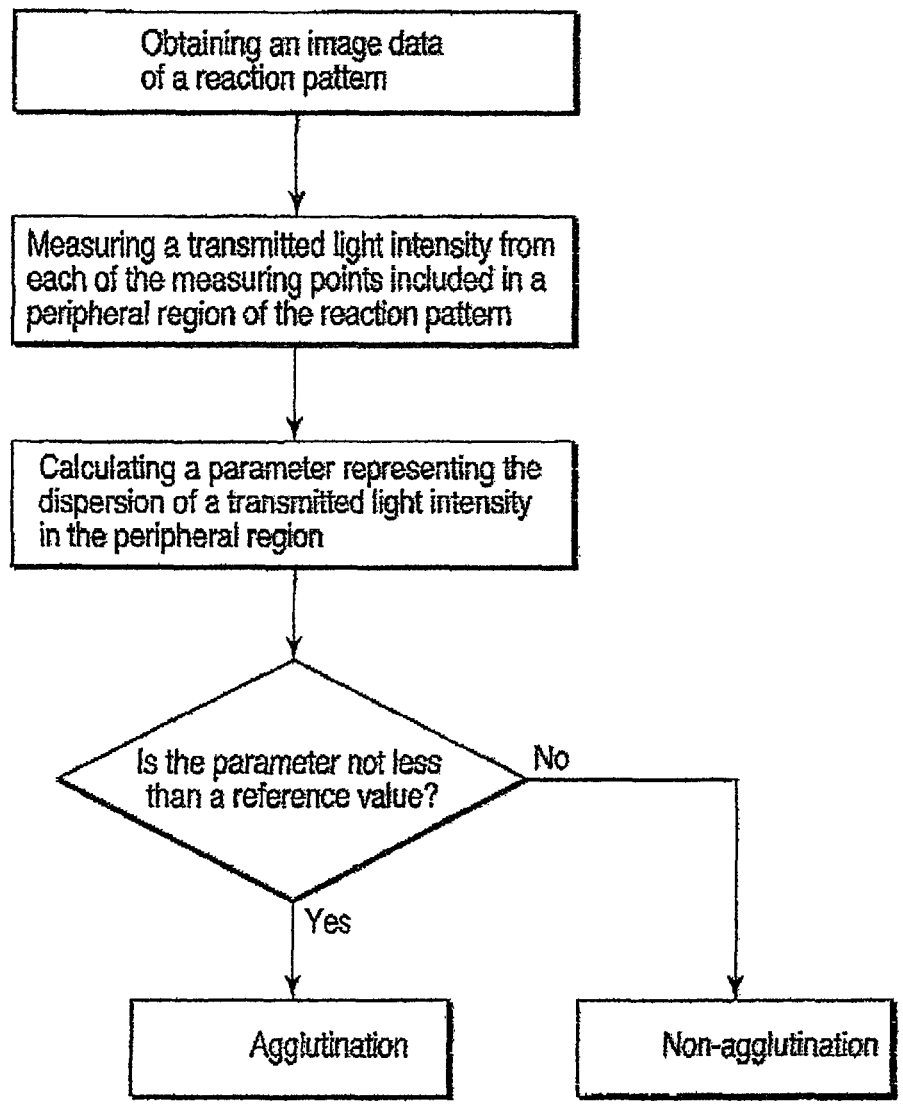
FIG. 6 is a flowchart of a process including calculating a parameter representing the dispersion of a transmitted light intensity in the peripheral region.

FIG. 5 shows a block diagram illustrating the construction of another example of the automatic agglutination image judgment apparatus used in carrying out the present invention. In this embodiment, by means of a light source 32 connected to a power source 31, a microplate 11 is spot-illuminated from the bottom side thereof through a group of lenses 33 and the light transmitted is received by a receptor 34. The output of this receptor 34 is converted into digital signals in a received light data processing section 35 and supplied to a data processing section 36. Further, the microplate 11 is enabled to move in a horizontal plane by means of a microplate-moving mechanism 37 under the control of the data processing section 36.

In this example, the data of the transmitted light intensity is obtained at each of the wells 11a and then, based on this data, the standard deviation of the transmitted light intensity or the range of the transmitted light intensity at the peripheral region of the reaction pattern created on the bottom of these wells 11a is calculated in the data processing section 36.

Next, the data processing in this data processing section 36 will be explained as one example wherein the standard deviation PSD is used.

In this data processing section 36, the data on the light intensity at each of pixels in a preset peripheral region 18 is acquired at first and then, based on this data, the standard deviation PSD of the transmitted light intensity at this peripheral region is calculated. Subsequently, this standard deviation PSD is compared with a predetermined reference value to thereby judge the agglutination or the non-agglutination.

After the reaction pattern has been judged in the data processing section 36 as described above, the judgment results are displayed on a display section 21, for example, in response to an instruction from an input section 38 such as a keyboard.

As described above, since the data of the transmitted light intensity in the peripheral region of the reaction pattern is extracted from the image data of the bottom of the well 11a to calculate the standard deviation thereof, and the agglutination/non-agglutination of the reaction pattern judged on the basis of the value of this calculated standard deviation, there is no possibility of mistaking the partial agglutination for the non-agglutination, thus making it possible to accurately judge the partial agglutination and to obtain judgment results excellent in reliability. Therefore, since it is no longer required to check and correct the judgment results by visual inspection by an operator or by other means as conducted in the prior art, the burden on an operator can be greatly alleviated.

EXAMPLE 1

As described above, FIG. 1A shows a diagram illustrating the reaction pattern of the partial agglutination image, and FIG. 1B shows a diagram illustrating the reaction pattern of the non-agglutination image. In these reaction patterns illustrated in these diagrams, the SPC value for judging the positive image is 17 in both cases. Herein, when a reference SPC value is preset for the purpose of judging that the partially agglutinated pattern of FIG. 1A is positive, the negative image of FIG. 1B may be also judged as positive.

However, in the case of the standard deviation PSD of the transmitted light intensity in the peripheral region that can be obtained according to the method of the present invention, the PSD value of the pattern of FIG. 1A is 14 and the PSD value of the pattern of FIG. 1B is 7, as shown in Table 1. Therefore, there is a clear difference in the PSD value between FIGS. 1A and 1B. Accordingly, by setting the reference value to 10 for example, the pattern of FIG. 1A can be judged as being the agglutination and the pattern of FIG. 1B can be judged as non-agglutination. By using the standard deviation PSD of the transmitted light intensity in the peripheral region according to the method of the present invention in this manner, it is now possible to realize accurate judgment of agglutination.

TABLE 1

| Reaction image | Partial agglutination image | Non-agglutination image |
|---|---|---|
| SPC | 17 | 17 |
| PSD of transmitted light intensity in the peripheral region | 14 | 7 |

EXAMPLE 2

Further, one embodiment wherein the range (maximum-minimum) of the data of the transmitted light intensity in the peripheral region is utilized will be explained. Table 2 represents the range (maximum-minimum) of the data of the transmitted light intensity in the peripheral region in the patterns of FIGS. 1A and 1B. The maximum value of the transmitted light intensity in the peripheral region in the pattern of FIG. 1A is 210 and the minimum value thereof is 126, so that the range is 84. On the other hand, the maximum value of the transmitted light intensity in the peripheral region in the pattern of FIG. 1B is 173 and the minimum value thereof is 135, so that the range is 38. Accordingly, by setting the reference value to 60 for example, the pattern of FIG. 1A can be judged as agglutination and the pattern of FIG. 1B can be judged as non-agglutination. By using the range of the transmitted light intensity in the peripheral region in this manner, it is also possible to accurately judge agglutination.

TABLE 2

| Reaction image | | Partial agglutination image | Non-agglutination image |
|---|---|---|---|
| SPC | | 17 | 17 |
| Transmitted light intensity in the peripheral region | Maximum | 210 | 173 |
| | Minimum | 126 | 135 |
| | Range | 84 | 38 |

As described above, according to the present invention, it is possible to automatically judge the partial agglutination and hence it is now possible to provide an agglutination judgment method which makes it possible to obtain a judgment result which is highly reliable. Accordingly, even in the clinical test, test results can be conveniently and rapidly obtained.

What is claimed is:

1. An agglutination judgment method of judging a type of a pattern using an apparatus, comprising:

obtaining an image of the pattern by a camera, the pattern being formed by particles in a liquid contained in a vessel, parts of the particles being gathered on a center region of a bottom of the vessel to form a first sub-pattern on the center region, remainders of the particles being distributed on a peripheral region of the bottom surrounding the center region to form second sub-patterns on the peripheral region, the peripheral region being divided from the center region by a boundary, each of the second sub-patterns having a smaller size than that of the first sub-pattern, and the apparatus comprising the camera, an image-processing circuit and a data-processing circuit;

processing the image by the image-processing circuit to obtain a distribution of transmitted light intensity for only the peripheral region on which the second sub-patterns are formed;

calculating a standard deviation for the distribution by the image-processing circuit; and comparing the standard deviation with a predetermined reference value by the data-processing circuit;

wherein the first sub-pattern is formed with aggregate constituted by two or more of the particles and each of the second sub-patterns is constituted by two or more of the particles in the agglutination pattern;

the first sub-pattern is formed with individual particles and each of the second sub-patterns is constituted by one of the particles in the non-agglutination pattern; and the first sub-pattern is formed with individual particles and each of the second sub-patterns is constituted by two or more of the particles in the partial agglutination pattern.

2. The method according to claim 1, further comprising:

judging the pattern by the data-processing circuit, judging the pattern including judging the pattern as an agglutination pattern when the standard deviation is greater than the predetermined reference value, and judging the pattern as a non-agglutination pattern when the standard deviation is smaller than the predetermined reference value.

3. The method according to claim 1, wherein the particles are red blood cells.

4. The method according to claim 3, further comprising:

judging the pattern by the data-processing circuit, judging the pattern including judging the pattern as an agglutination pattern when the standard deviation is greater than the predetermined reference value, and judging the pattern as a non-agglutination pattern when the standard deviation is smaller than the predetermined reference value.

5. The method according to claim 4, wherein each of the second sub-patterns is constituted by two or more of the red blood cells in the agglutination pattern, and each of the second sub-patterns is constituted by one of the red blood cells in the non-agglutination pattern.

* * * * *